US012779164B2

(12) United States Patent
Schuster

(10) Patent No.: US 12,779,164 B2
(45) Date of Patent: Nov. 3, 2026

(54) VENTILATOR

(71) Applicant: Loewenstein Medical Technology S.A., Luxembourg (LU)

(72) Inventor: Jan Schuster, Schwalbach am Taunus (DE)

(73) Assignee: Loewenstein Medical Technology S.A., Luxembourg (LU)

( * ) Notice: Subject to any disclaimer, the term of this patent is extended or adjusted under 35 U.S.C. 154(b) by 1359 days.

(21) Appl. No.: 16/855,136

(22) Filed: Apr. 22, 2020

(65) Prior Publication Data

US 2020/0338297 A1 Oct. 29, 2020

(30) Foreign Application Priority Data

Apr. 25, 2019 (DE) ........................ 102019110740.7

(51) Int. Cl.

| | |
|---|---|
| ***A61M 16/10*** | (2006.01) |
| ***A61L 2/084*** | (2026.01) |
| ***A61L 2/085*** | (2026.01) |
| ***A61L 2/26*** | (2006.01) |
| ***A61L 9/18*** | (2006.01) |
| ***A61M 16/00*** | (2006.01) |

(Continued)

(52) U.S. Cl.

CPC ......... *A61M 16/1055* (2013.01); *A61L 2/084* (2013.01); *A61L 2/085* (2013.01); *A61L 2/26* (2013.01); *A61L 9/18* (2013.01); *A61M 16/0057* (2013.01); *A61M 16/06* (2013.01); *A61M 16/0816* (2013.01); *A61L 2202/11* (2013.01); *A61L 2202/24* (2013.01); *A61L 2209/12* (2013.01); *A61L 2209/14* (2013.01); *A61M 2202/203* (2013.01); *A61M 2202/206* (2013.01)

(58) Field of Classification Search

CPC .......... A61L 2/084; A61L 2/085; A61L 2/088; A61L 2/10; A61L 2/26; A61L 9/18; A61L 9/20; A61L 9/205; A61L 2202/11; A61L 2202/24; A61L 2209/12; A61L 2209/14; A61M 16/0057; A61M 16/06; A61M 16/0816; A61M 16/1055

See application file for complete search history.

(56) References Cited

U.S. PATENT DOCUMENTS

| | | | |
|---|---|---|---|
| 3,126,003 | A | 3/1964 | Steel |
| 5,855,203 | A | 1/1999 | Matter |
| 2006/0177356 | A1 | 8/2006 | Miller |

(Continued)

FOREIGN PATENT DOCUMENTS

| | | | |
|---|---|---|---|
| CN | 204233560 | U | 4/2015 |
| DE | 2347791 | A1 | 4/1975 |

(Continued)

OTHER PUBLICATIONS

Sliney, D. "What is light? The visible spectrum and beyond." Eye 30, 222â229 (2016). https://doi.org/10.1038/eye.2015.252 (Year: 2016).*

*Primary Examiner* — Timothy C Cleveland
(74) *Attorney, Agent, or Firm* — Abel Schillinger, LLP

(57) ABSTRACT

The invention relates to a ventilator which comprises a pneumatic system for conveying ventilation gas in a flow direction (d) to a patient or from a patient, and further comprises at least one light source which is directed, in emission direction (r), at the ventilation gas and/or at a display area and/or at the pneumatic system.

19 Claims, 11 Drawing Sheets

(51) Int. Cl.
*A61M 16/06* (2006.01)
*A61M 16/08* (2006.01)

(56) References Cited

U.S. PATENT DOCUMENTS

| | | | | |
|---|---|---|---|---|
| 2007/0163588 | A1 | 7/2007 | Hebrank et al. | |
| 2008/0032119 | A1 | 2/2008 | Feldhahn et al. | |
| 2008/0170971 | A1* | 7/2008 | Bergeron | A61L 9/22<br>422/186.04 |
| 2012/0174922 | A1 | 7/2012 | Virr et al. | |
| 2015/0129781 | A1 | 5/2015 | Kretschmann | |
| 2016/0038621 | A1 | 2/2016 | Victor et al. | |
| 2016/0271288 | A1 | 9/2016 | Davis | |
| 2016/0317685 | A1 | 11/2016 | Pujolet et al. | |
| 2016/0317832 | A1 | 11/2016 | Barneck et al. | |
| 2017/0028089 | A1 | 2/2017 | Garrett | |
| 2017/0326326 | A1 | 11/2017 | Hansmann et al. | |
| 2018/0104374 | A1 | 4/2018 | Kim et al. | |
| 2018/0339073 | A1* | 11/2018 | Clynne | A61L 2/0047 |

FOREIGN PATENT DOCUMENTS

| | | | |
|---|---|---|---|
| DE | 10107443 | A1 | 8/2002 |
| GB | 1488018 | A | 10/1977 |
| WO | 2011006206 | A1 | 1/2011 |
| WO | 2012052908 | A1 | 4/2012 |
| WO | 2014159874 | A1 | 10/2014 |
| WO | 2015092695 | A1 | 6/2015 |
| WO | 2017023783 | A1 | 2/2017 |

* cited by examiner

VENTILATOR

CROSS-REFERENCE TO RELATED APPLICATIONS

The present application claims priority under 35 U.S.C. § 119 of German Patent Application No. 102019110740.7, filed Apr. 25, 2019, the entire disclosure of which is expressly incorporated by reference herein.

BACKGROUND OF THE INVENTION

1. Field of the Invention

The invention relates to a ventilator. Within the scope of the present invention, a ventilator is understood to mean a controlled apparatus, for example an apparatus electronically controlled by microprocessors, which is embodied to support or maintain the respiratory function of a patient or to treat said respiratory function by therapy (e.g., CPAP therapy). This also includes those ventilators embodied as anesthesia appliances and/or for ventilating patients without spontaneous respiration. Here, the patient is a human or an animal that breathes air, for example a mammal.

2. Discussion of Background Information

The transmission of infectious diseases by pathogens, i.e., infectious microorganisms such as, e.g., fungi, fungal spores, bacteria and viruses, is predominantly implemented through the air. In public buildings with large numbers of people, in particular hospitals, the concentration of pathogens in the ambient air, and hence the risk of infection, is particularly high. People with a weakened immune system are particularly affected thereby. Here, a possible path of infection leads via the air from the pressurized gas lines, which is applied or added by way of ventilators or conveyed from the appliance surroundings by means of a fan.

Therefore, ventilators, even those embodied as anesthesia appliances, are provided with particle filters for separating out pathogens as a standard. Since these filters are based on the principle of size exclusion, not all pathogens are separable in this case. Thus, the risk of pneumonic infections is not sufficiently averted in such ventilators according to the prior art.

The disinfecting action of ultraviolet radiation (UV) was discovered by the Austrian physician Gustav Kaiser in 1902, with ultraviolet radiation comprising wavelength ranges from 100 nm to 280 nm (UV-C), from 280 nm to 315 nm (UV-B) and from 315 nm to 380 nm (UV-A). By way of example, US 2016/0271288 A1, the entire disclosure of which is incorporated by reference herein, has described an apparatus embodied for the sterilization of air by means of UV.

A further apparatus for disinfecting microorganisms in general by means of polychromatic light is disclosed in WO 2017/023783 A1, the entire disclosure of which is incorporated by reference herein. Here, the polychromatic light has a significant wavelength component of ultraviolet radiation, for the generation of which a single light source is provided. Therefore, the apparatus claimed in WO 2017 023783 A1 requires a dichroic mirror for deriving thermal radiation and for reflecting back radiation with an antimicrobial effect.

Consequently, there has been no lack of proposals either for freeing the respiratory air or respiratory air mixture applied by ventilators from pathogens by means of UV, i.e., for disinfecting said respiratory air or respiratory air mixture. WO 2014/159874 A1, the entire disclosure of which is incorporated by reference herein, teaches an UV irradiation system which comprises optical fibers for emitting UV light, which have been introduced into medical tubes, for example a tracheal tube. WO 2012/052908 A1, the entire disclosure of which is incorporated by reference herein, likewise discloses a tracheal tube with such optical fibers, which preferably emit electromagnetic radiation in the wavelength range of UV-C. WO 2015/092695 A1, the entire disclosure of which is incorporated by reference herein, comprises a ventilator, an illumination apparatus for emitting generally disinfecting light being integrating in the pneumatic circuit system thereof, the disinfecting light preferably being given by UV and particularly preferably by UV-C therein and being provided, inter alia, by light sources (LED). DE 101 07 443 A1, the entire disclosure of which is incorporated by reference herein, relates to a method for disinfecting conveyed respiratory air in ventilators by means of strong electromagnetic radiation within the pneumatic circuit systems thereof, wherein the electromagnetic radiation is given by UV or microwaves and applied in pulsed form. By contrast, CN 204233560 U, the entire disclosure of which is incorporated by reference herein, describes an anesthesia appliance with a disinfecting condensate outflow, with, in complementary fashion to the aforementioned examples, only the expiration tube being connected, in sequence, with an expiration check valve, a photocatalyst sterilizer and a cold trap. Although CN 204233560 U discloses the application of UV for disinfection in general, it does not disclose the nature and mode of operation of the photocatalyst sterilizer.

Ventilators including anesthesia appliances according to the prior art, which are embodied to disinfect conveyed respiratory air or a conveyed respiratory air mixture by means of UV, have the following substantial disadvantages:

- Purely irradiating the conveyed respiratory air or a conveyed respiratory air mixture is insufficient for killing pathogens since, to this end, the flows to be chosen for ventilation are much too high and the pathogens transported with the conveyed respiratory air or their conveyed respiratory air mixture are consequently exposed for an irradiation duration that is too short.
- Ultraviolet radiation (UV), particularly in the UV-B wavelength range and especially in the UV-C wavelength range, damages irradiated components, especially those made of plastic.
- UV, particularly in the UV-B wavelength range and especially in the UV-C wavelength range, causes radical dissociation reaction of inhalation anesthetics to a significant extent, in particular of halogenated derivatives such as halothane, isoflurane, sevoflurane and desflurane. Here, the radicals formed are highly toxic to the ventilated patient.
- Ultraviolet radiation (UV) in the UV-B wavelength range additionally causes the formation of singlet oxygen and ozone from the triplet oxygen of the conveyed respiratory air or of the conveyed respiratory air mixture. Singlet oxygen and ozone are likewise highly toxic to the ventilated patient.
- Ultraviolet radiation (UV) possibly emerging from the ventilator represents a significant risk to health, both for the operating staff and the patient.

Light sources, a light-emitting diode is mentioned by example, are commercially available with various wide emission ranges and emission maxima, from the UV to the infrared (IR) range, and available in virtually any shape or size. Light sources are cost-effective and have optimal efficiency in relation to other electric illuminants. Each light source has an emission surface, which is embodied to emit light. Thus, the design of the shape of the emission surface renders both the light emission direction and the geometric emission form of the emitted light adjustable, for example as a light cone or as a light fan. Light sources each emit polychromatic light over a wavelength interval and have at least one emission maximum in respect of the intensity for a specific wavelength within such a wavelength interval, with each intensity profile in respect of a respective emission maximum corresponding to Planck distribution in each case.

In view of the foregoing, it would be advantageous to have available a ventilator and/or a corresponding adapter, which is improved over the prior art in respect of hygiene and operational safety.

SUMMARY OF THE INVENTION

The present invention provides a ventilator and an adapter for a ventilator as set forth in the instant independent claims.

In particular, the present invention provides the following items:

1. A ventilator comprising a pneumatic system for conveying ventilation gas in a flow direction to a patient or from a patient, the ventilator comprising at least one light source, which is directed, in an emission direction, at the ventilation gas and/or at a display area and/or at the pneumatic system.

2. The ventilator according to item 1, wherein the emitted light is selected from a first wavelength range of 385 nm to 780 nm and/or from a second wavelength range of more than 780 nm to 2000 nm;

3. The ventilator according to items 1 or 2, wherein the light source is configured and embodied to at least weaken or inactivate germs (viruses, bacteria, fungi) by way of the emitted light.

4. The ventilator according to any one of items 1 to 3, wherein the pneumatic system comprises at least one air supply to the ventilator and/or a respiratory gas outflow from the patient and/or a patient interface and/or a gas flow line and/or filters.

5. The ventilator according to any one of items 1 to 4, wherein the at least one light source is disposed in the region of the air supply to the ventilator and/or in the region of the respiratory gas outflow from the patient and/or in the region of patient interface and/or along the gas flow lines.

6. A ventilator comprising a pneumatic circuit system for conveying ventilation gas in a flow direction to a patient, wherein at least one particle filter is disposed within the pneumatic circuit system, at least one light source being directed at said particle filter in a light emission direction.

The ventilator may also be characterized in that the light source is disposed first in the flow direction, followed by the particle filter.

The ventilator may also be characterized in that light emitted toward the particle filter is selected from a first wavelength range of 385 nm to 780 nm and/or from a second wavelength range of more than 780 nm to 2000 nm.

The ventilator may also be characterized in that at least one light source is disposed in each case on both sides of the particle filter.

The ventilator may also be characterized in that the entire area of the particle filter is able to be illuminated on the side of the light source.

The ventilator may also be characterized in that the particle filter is able to be illuminated in all round uniform fashion.

The ventilator may also be characterized in that a plurality of types of light sources are directed in circumferential fashion at the particle filter in an alternating sequence with respect to the types of light sources, the types of light sources differing in terms of the respectively emitted light.

The ventilator may also be characterized in that one type of such light sources embodied to emit light with an emission maximum at 405 nm is provided.

The ventilator is also characterized in that the emitted light of all light sources comprises a wavelength continuum from 385 nm to 2000 nm.

The ventilator may also be characterized in that the particle filter is embodied as a glass frit or as a pellet made of glass wool and/or as a filter for retaining pathogens and dust.

The ventilator may also be characterized in that a plurality of particle filters with a pore size respectively decreasing in the flow direction are disposed in the pneumatic circuit system.

Also provided by the present invention is an adapter for a ventilator with a pneumatic system for conveying ventilation gas. The pneumatic system comprises at least an air supply to the ventilator and/or a respiratory gas outflow from the patient and/or a patient interface and/or a gas flow line and/or filters. The adapter is equipped with at least one light source and is able to be connected to the air supply and/or the respiratory gas outflow and/or the patient interface and/or a gas flow line. At least one light source can be directed at the ventilation gas and/or the pneumatic system and the at least one light source is configured and embodied in such a way that germs (viruses, bacteria, fungi) are at least weakened or inactivated by the emitted light.

The adapter may comprise at least one device for slowing the flow of the ventilation gas and/or for at least temporarily accumulating and/or filtering germs (viruses, bacteria, fungi) and the at least one light source may be directed at this device.

The at least one device may be embodied in the form of a particle filter and/or a baffle and/or a cover.

The ventilator may have a pneumatic circuit system for conveying ventilation gas in a flow direction by means of a gas conveying apparatus, through an appliance outlet and via an interface to a patient. The gas conveying apparatus is provided by an electric fan for sucking in external air or by a connector to a pressurized air supply apparatus. In the present invention, an interface is understood to mean a connection apparatus that pneumatically connects the appliance outlet to the respiratory organs of the patient. By way of example, the interface is provided by a ventilation tube that is connected to a tracheal tube, with the tracheal tube being guided directly to the respiratory organs of the patient. By way of example, the ventilation tube is alternatively connected to a ventilation mask, with the ventilation mask being placed in all-round seating fashion on the mouth and/or nose of the patient and consequently being connected to the respiratory organs of the patient. The pneumatic circuit system comprises the entire piping for the flow of respiratory gas, the pipes of which are pneumatically interconnected between the gas conveying apparatus and the appliance outlet. If the claimed ventilator is embodied only for the ventilation of a patient, the ventilation gas consists of natural or synthetic air or natural or synthetic air enriched with additional oxygen or pure oxygen. If the claimed ventilator is additionally embodied as an anesthesia appliance, at least one inhalation anesthetic is admixed, at least on a temporary basis, to the ventilation gas. In both embodiments of the claimed ventilator, additional gaseous and/or aerosolized water and/or one or more noble gases are selectively admixed to the ventilation gas. Here, the flow direction of the ventilation gas is set in the direction from the gas conveying apparatus to the appliance outlet. During the operation of the claimed ventilator, the ventilation gas is typically conveyed by means of the gas conveying apparatus with a flow of up to 300 ml $min^{-1}$.

At least one such particle filter that has at least one light source directed thereat in a light emission direction is pneumatically switched within the pneumatic circuit system in the claimed ventilator.

The particle filter has a front surface and a back surface, with the particle filter being pneumatically switched in the pneumatic circuit system in such a way that, during the operation of the claimed ventilator, the flow of the ventilation gas in the flow direction penetrates the front surface first, followed by the back surface of the particle filter. Consequently, the front surface and the back surface each substantially or entirely correspond to a flow cross section. Such an arrangement of the particle filter within the pneumatic circuit system is based on a first inventive concept, namely that pathogens are slowed down in terms of their flow speed during the flow of the ventilation gas through the particle filter; in this case, it is irrelevant whether the pathogens are completely or partly or not at all held back during a flow of the ventilation gas through the particle filter. Purely slowing the pathogens down provides a sufficient time interval for partly or completely killing the pathogens by irradiation with light, or at least weakening these in terms of their virulence or neutralizing them. Thus, what is decisive is the accumulation of pathogens in front of and on the front surface of the particle filter. By contrast, when the pathogens pass through the back surface, they do not accumulate there; instead, these pathogens that have passed through are carried away by the flow of the respiratory gas.

A second inventive concept is therefore realized in the proposed ventilator by way of directing at least one light source at the particle filter in a light emission direction in such a way that, in the flow direction, the light source is securely disposed first, followed by the particle filter. Consequently, an emission of light on the front surface of the particle filter by means of the light source is brought about within the pneumatic circuit system. This results in an irradiation of both the pathogens accumulated on the front surface and of the pathogens deposited on the front surface, in the light emission direction of the light source. By way of example, in the case of an appropriately manufactured particle filter made of an at least partly translucent material, penetration of the light emitted by the light sources through the front surface is facilitated, and so even pathogens within the particle filter are at least partly captured by the irradiation.

The proposed ventilator by no means requires the light source to be attached within the piping of the pneumatic circuit system. All that is needed is that the light emission direction of the light source is directed at the front surface of the particle filter and an irradiation of the front surface is ensured. By way of example, this is also realizable by way of a sufficiently transparent light window, which is let into the piping in front of the front surface of the particle filter. By way of example, such a light window is manufactured from quartz or sapphire. By way of example, the light source is affixed to the light window in such a way that, in the light emission direction, an irradiation of the front surface of the particle filter is rendered possible. By avoiding the arrangement of the light source within the piping, the formation of a disadvantageous flow resistance is thus eliminated at the same time, and so a laminar flow of the ventilation gas is particularly advantageously realizable within the piping. Further, in the case of multi-part manufacturing of the piping and the light source being held, such an apparatus is particularly advantageously designable in such a way that the light source is easily removable for simple maintenance or possible repair of the claimed ventilator, without opening of the piping being necessary.

In respect of the light emitted by the light source, the proposed ventilator is based on the hierarchy of coupled quantum systems as third inventive concept. As a consequence of this, a set of different oscillators states is respectively given for each electronic excitation state of a molecule or an aggregate of molecules. A pathogen, i.e., a virulent microorganism, corresponds in principle to an aggregate of molecules. If the bond order of a chemical bond is reduced in the case of such an aggregate of molecules by electronic excitation as a result of irradiation with light selected from a first wavelength range from 385 nm to 780 nm, and in particular from a first wavelength range from 385 nm to 425 nm, this results in energetically reduced oscillator states and hence energetically reduced dissociation energies of the relevant bond in the case of a real given Morse potential. Consequently, accelerated dissociation of the relevant bond is realizable in the case of simultaneous irradiation with infrared radiation (IR), selected from a second wavelength range of more than 780 nm to 2000 nm. Experiments on pathogens have shown that accelerated killing or at least an accelerated inactivation of pathogens in respect of the virulence thereof is obtainable in the case of irradiation with light containing light both from the first wavelength range and from the second wavelength range. By contrast, there is significantly slower killing or significantly slower inactivation of pathogens in the case of irradiation with light, which in each case only contains only the first wavelength range or only the second wavelength range.

Therefore, the light emitted toward the particle filter in the proposed ventilator is selected from a first wavelength range from 385 nm to 780 nm (sufficient excitation of electronic states) and from a second wavelength range from more than 780 nm to 1700 nm (corresponding to an excitation of oscillator states).

Advantageous developments of the proposed ventilator in respect of an arrangement of light sources and the nature thereof are discussed below. These developments correspond to incremental optimizations of the claimed ventilator in respect of intensity and efficiency of the illumination of the particle filter.

In a first development of the invention in respect of the light sources, at least one light source is disposed in each case on both sides of the particle filter. Consequently, at least one light source is directed at the particle filter, even on the back surface thereof, in the light emission direction of said light source, as a result of which a post-treatment of pathogens that have passed through the particle filter is particularly advantageously facilitated by way of irradiation with light. By way of example, if the particle filter in this case is not only manufactured from translucent material but if its front surface and its back surface also have a sufficiently small distance from one another, then, particularly advantageously, irradiation over the entire distance between back and front surface is additionally facilitated in the case of a light source with sufficient radiation power.

In a second development of the invention in respect of the light sources, the entire area of the particle filter is able to be illuminated on the side of the light source. By way of example, this can already be brought about with respectively one light source by virtue of said light source being embodied to emit light in the geometric form of a light cone with a sufficiently large light cone angle. Consequently, it is possible during the operation of the proposed ventilator to irradiate all pathogens that strike the front surface of the particle filter and/or emerge through the back surface of said particle filter with the flow of the ventilation gas.

In a third development of the invention in respect of the light sources, the particle filter is able to be illuminated in all round uniform fashion by means of at least one light source. By way of example, in the case of a single light source, this can be brought about by virtue of the emission surface thereof itself having a circumferential, closed and inwardly angled embodiment. By way of example, a circumferential, closed light window is introduced in the piping, above which a light source with a circumferential, closed and inwardly angled emission surface is placed and secured. As an alternative to one light source, a plurality of light sources are disposed equidistantly from one another in each case around the particle filter, for example. A uniform illumination of the front and/or back surface of the particle filter ensures that all pathogens striking the particle filter or passing through the particle filter are exposed to the same, or at least approximately the same, radiance of the light emitted by the light source or light sources.

Using a light source which, for example, is embodied to emit light in a wavelength interval from 385 nm to 1700 nm, preferably to 2000 nm, and which only has a single emission maximum, an at least approximately uniform excitation of both electron states and oscillator states is only achievable if the emission maximum is located between the wavelength range of the excitation of electron states and the wavelength range of the excitation of oscillator states. For sufficient high excitation, this requires a light source with a very high performance.

If, for the purposes of irradiating the particle filter, only one type of light sources is provided for emitting light in a wavelength interval from 385 nm to 2000 nm and embodied accordingly, light sources of this type therefore preferably respectively have at least one emission maximum, both in the first wavelength range of the excitation of electron states and in the second wavelength range of the excitation of oscillator states. That is to say, a light source of this type has a total of at least two emission maxima over a wavelength interval from 385 nm to 2000 nm. In the case of light sources of such a type, an at least approximately uniform excitation of both electron states and oscillator states, and hence efficient killing and/or deactivation of pathogens, is already achievable with a comparatively low performance.

In a fourth development of the invention in respect of the light sources, a plurality of types of light sources are directed in circumferential fashion at the particle filter in an alternating sequence with respect to the types of light sources. Here, the types of light sources differ in terms of the respectively emitted light. This particularly advantageously allows the choice and combination of those light sources whose respective emitted light is matched in terms of wavelength interval and/or emission maximum to the excitation of electron states and/or oscillator states. Consequently, this also renders it possible to adapt the illumination of the particle filter in targeted fashion in respect of killing and/or inactivation of specific pathogens, such as MRSA, for example. By arranging different types of light sources in circumferential fashion around the particle filter and in an alternating sequence, an illumination of the particle filter that covers the entire area and is uniform can be realized in simple fashion.

In a fifth development of the invention in respect of the light sources, one type of such light sources embodied to emit light with an emission maximum at 405 nm is provided. In respect of the electronic excitation of a large number of types of pathogens, irradiation with light at a wavelength of 405 nm was found to be optimal. Particularly high-performance light sources to this end are embodied to emit light in a wavelength interval restricted to 385 nm to 425 nm, with an emission maximum at 405 nm.

In a sixth development of the invention in respect of the light sources, the emitted light of all light sources comprises a wavelength continuum from 385 nm to 2000 nm. This ensures the excitation of all electrons and oscillator states. By way of example, this is realized by three types of light sources, wherein, in each case,

- the light sources of the first type are embodied to emit light in a wavelength interval restricted to 385 nm to 425 nm, with an emission maximum at about 405 nm,
- the light sources of the second type are embodied to emit light in a wavelength interval restricted to 385 nm to 1000 nm, with an emission maximum at about 600 nm, and
- the light sources of the third type are embodied to emit light in a wavelength interval restricted to 900 nm to 2000 nm, with a first emission maximum at about 1400 nm and a second emission maximum at about 1600 nm.

Advantageous embodiments of the proposed ventilator in respect of the particle filter are discussed in more detail below. By no means is the proposed ventilator restricted to a particle filter disposed in the pneumatic circuit system, in particular to one or more particle filters of only one type. Nor is the proposed ventilator restricted in any case to particle filters disposed in the pneumatic circuit system, with at least one light source being directed at each said particle filter in a light emission direction. The number and nature of the particle filters is only set by an installation size, to be observed, of the claimed ventilator and by the specification of a maximum overall flow resistance of up to about 5 hPa min $120^{-1}$ $L^{-1}$, for example.

In a first embodiment of the invention with respect to the particle filter, the particle filter is embodied as a glass frit or as a pellet made of glass wool and/or for retaining pathogens. A glass frit or a pellet made of glass wool is particularly advantageously sterilizable by autoclaving at more than 130° C., and hence reusable. A size selectivity in respect of the retention of specific microorganisms and hence pathogens, for example bacteria, fungi and viruses, is adjustable by way of a choice of a pore dimension of the particle filter. A type selectivity of the particle filter in respect of the retention of specific microorganisms is likewise alternatively or additionally optimizable by a choice of a filter material, for example Teflon or nylon or a hydrophobic or hydrophilic plastic in fiber form. Particle filters with very different pore dimensions and manufactured from very different materials for the retention of particles and/or microorganisms are commercially available on the market. The disinfection of the ventilation gas is additionally improved by a permanent retention of particles and/or microorganisms in the particle filter.

In a further variant of the second embodiment of the invention in respect of the particle filter, the glass frit has a pore width of from about 1 μm to about 200 μm, preferably of from about 2 to about 150 μm. Such a glass frit has no noticeable flow resistance, without the accumulation of microorganisms in front of and on the front surface of the glass frit being impaired.

In a third embodiment of the invention with respect to the particle filter, a plurality of particle filters with a pore size respectively decreasing in the flow direction are disposed in the pneumatic circuit system. Such a combined arrangement ensures an optimum use duration of the particle filter before replacement of the latter is required on account of saturation with particles and microbes.

In some embodiments of the invention, the light sources are supplied with power via the power supply unit of the ventilator. To this end, the light sources are integrated into the internal power grid of the ventilator, for example. This integration for example also facilitates the operation of the light sources in the case where the ventilator is supplied with power by way of an accumulator.

In some embodiments, the light sources are supplied with power by way of an external power source—in relation to the ventilator. Thus, the light sources can be connected to a dedicated power supply unit or to accumulators or batteries, for example. The connection to an external power supply is conceivable, particularly for the adapter according to the invention. However, connecting the light sources to an external power source is conceivable even for light sources installed in the ventilator.

In further embodiments of the invention, the light sources are configured to be switchable, i.e., activatable and deactivatable. By way of example, the light sources are connected to a switch that, for example, can interrupt the power supply, i.e., can turn off or deactivate the light sources. Such a switch is configured in such a way that a (renewed) activation of the light sources or turning on of the light sources is also facilitated. By way of example, such a light switch can be integrated in the housing of the ventilator or else be embodied as an extra switch. By way of example, the adapter according to the invention has a switch that is independent of the ventilator.

In a further embodiment, the light sources are configured in such a way that they are variable in terms of their luminosity (for example, by adapting the operating voltage of the light sources), i.e., dimmable, by way of a control unit not described in any more detail. This should also be understood to mean that the luminosity or the operating voltage of the light sources can be down-regulated so far that the light sources are switched off.

In one embodiment, the light sources are configured and integrated into the ventilator in such a way that said light sources can be switched on and off by a control system of the ventilator and can also be varied in terms of luminosity. By way of example, this can set up an automatic deactivation of the lamps when transferring the ventilator from power grid operation to accumulator operation.

The claimed ventilator has the following advantages over ventilators according to the prior art:

- The light emitted by the light sources is detrimental neither to the manufacturing material of the piping nor to humans and mammals in respect of the wavelengths.
- Hence, technically complicated measures for protection against damaging electromagnetic radiation and for dissipating excess heat are dispensed with in the proposed ventilator.
- Toxic substances do not form from the ventilation gas in the case of an emitted light in a wavelength range of 385 nm to 2000 nm, even if said ventilation gas contains an inhalation anesthetic such as, for example, halothane, isoflurane, sevoflurane and desflurane.
- The proposed ventilator is substantially improved over the prior art in respect of simple manufacturing, economical operation, hygiene and operational reliability.

Moreover, the provision of an adapter for ventilators offers the advantage of cost-effectively retrofitting ventilators without the described features of the invention with specifically those features. The proposed adapter comprises the same features as the proposed ventilator and, moreover, can be subsequently or additionally attached or connected to a ventilator.

The terms pathogens, germs and microorganisms are used synonymously in this application, in order to denote, particularly but not exclusively, viruses, bacteria and fungi, for example.

BRIEF DESCRIPTION OF THE DRAWINGS

The proposed ventilator is described in more detail below on the basis of the accompanying drawings, in which.

DETAILED DESCRIPTION OF EXEMPLARY EMBODIMENTS OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

In the following exemplary embodiment, the claimed ventilator 1 is embodied as an anesthesia appliance. The ventilator 1 has a pneumatic circuit system 2 for conveying ventilation gas in a flow direction d by means of an electric fan, through an appliance outlet and via an interface to a patient. The interface is provided by a ventilation tube that is connected to a tracheal tube, with the tracheal tube being guided directly to the respiratory organs of the patient. FIG.

Figure 1:
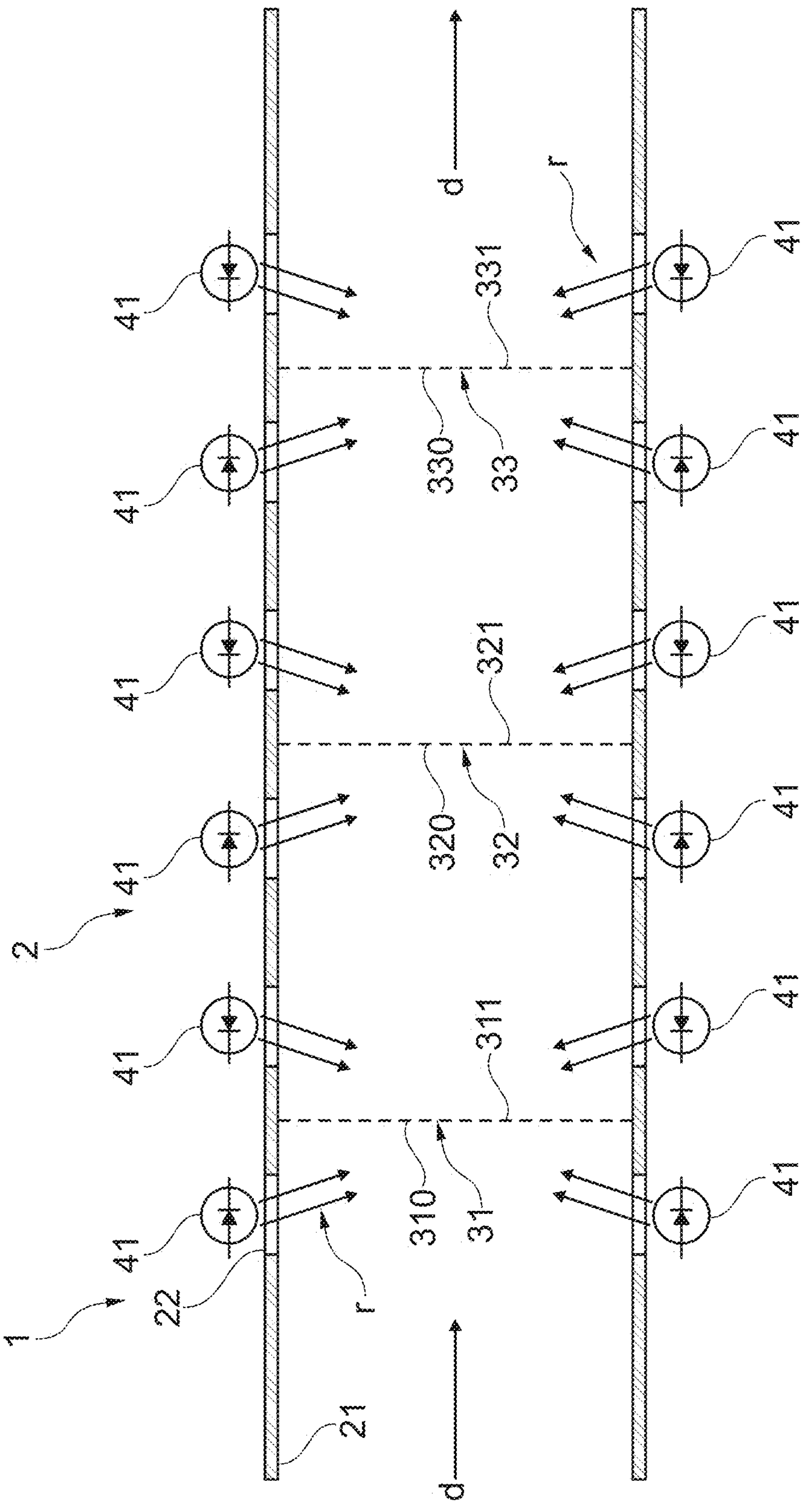
FIG. 1 shows a longitudinal section of the claimed ventilator in a schematic partial view of a pneumatic circuit system.
Figure 2:
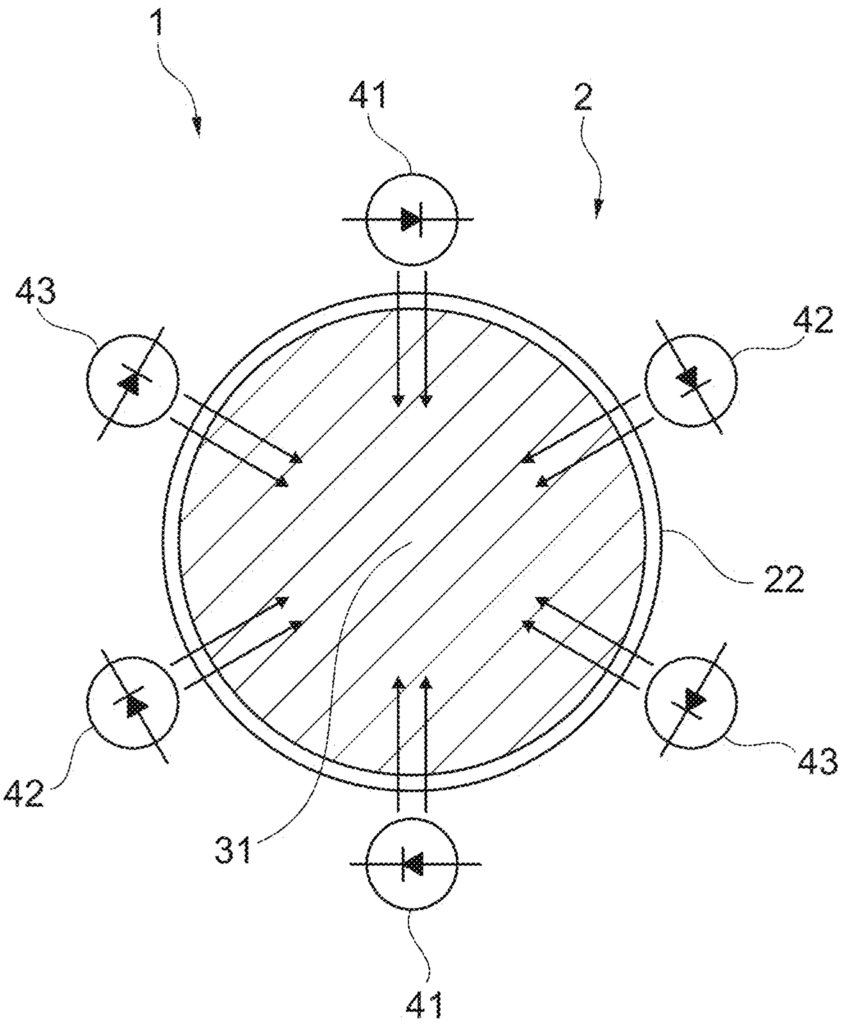
FIG. 2 shows a cross section through the pneumatic circuit system.

1 and FIG. 2 are not true to scale. FIG. 1 and FIG. 2 do not show the electric fan, the appliance outlet, the interface, the respiratory organs of the patient and the patient. In order to elucidate the general construction principle and functionality, FIG. 1 and FIG. 2 each show schematic partial views of the claimed ventilator 1.

Three particle filters 31, 32 and 33 are pneumatically connected within the pneumatic circuit system 2. Six light sources are disposed in each case on both sides of each particle filter 31, 32 and 33, the light sources comprising those of a first type 41, a second type 42 and a third type 43. The light sources 41, 42 and 43 are directed toward the particle filters 31, 32 and 33, in a light emission direction r in each case. FIG. 1 and FIG. 2 elucidate the light emission directions r in the form of a dual arrow in each case.

FIG. 1 shows a longitudinal section of the claimed ventilator 1 in a schematic partial view of a pneumatic circuit system 2. Within the pneumatic circuit system 2, the one to three particle filters 31, 32 and 33 are pneumatically connected, for example within cylindrical piping 21. The particle filters 31, 32 and 33 each have a front surface 310, 320 and 330 and each have a back surface 311, 321 and 331, the particle filters 31, 32 and 33 being pneumatically connected in the pneumatic circuit system 2 in such a way that, during operation of the claimed ventilator 1, the flow of ventilation gas in the flow direction d initially penetrates the respective front surface 310, 320 and 330 of the respective particle filter 31, 32 and 33, followed by the respective back surface 311, 321 and 331. The flow direction d is elucidated by an arrow in FIG. 1. Consequently, the front surfaces 310, 320 and 330 and the back surfaces 311, 321 and 331 each substantially correspond to a flow cross section.

A total of six light windows 22 are securely let into the piping 21 by way of a tongue and groove connection. The light windows 22 are likewise embodied as a cylindrical pipe section in each case, which, in addition to two connecting tongues on each connection side, has the same radius and wall thickness as the piping 21. The consequently circumferential, closed light windows 22 are identical in terms of form and manufactured from quartz. In the flow direction d, a light window 22 is in each case disposed upstream and in each case disposed downstream of each particle filter 31, 32 and 33.

Only the light sources of the first type 41 are visible in FIG. 1. A total of six light sources 41, 42 and 43 are affixed to each light window 22 in such a way that, in each case in the light emission direction r, an irradiation of both the respective front surface 310, 320 and 330 and the respective back surface 311, 321 and 331 of the relevant particle filter 31, 32 and 33 is facilitated. Consequently, the light sources 41, 42 and 43 are precluded from influencing a laminar flow of the ventilation gas on account of the design in the partial section of the piping 21 shown in FIG. 1. In this exemplary embodiment of the claimed ventilator 1, an irradiation of the pathogens both during the accumulation thereof in front of the front surface 310, 320 and 330 and during the passage through the back surface 311, 321 and 331 of the particle filters 31, 32 and 33 is thus facilitated on account of the design and in particularly advantageous fashion.

By way of example, the particle filter 31 is embodied as a glass frit 31. By way of example, silver or titanium dioxide is additionally introduced into the glass frit 31, with the titanium dioxide containing platinum with a mass fraction of 1%. Consequently, the glass frit 31 is embodied as a catalyst, which accelerates the oxidation of microorganisms in both photocatalytic and thermocatalytic fashion; hence, a decomposition, killing and/or inactivation of microorganisms is realizable in three mutually independent ways in this exemplary embodiment. The glass frit 31 has a pore width of 1 μm to 200 μm and consequently represents a negligible flow resistance under operating conditions. The particle filter 32 is embodied to retain bacteria and fungi and the particle filter 33 is embodied to retain viruses. Consequently, three particle filters 31, 32 and 33 with a respectively decreasing pore dimension in the flow direction d are disposed in the pneumatic circuit system 2.

FIG. 2 shows a cross section of the claimed ventilator 1 in a schematic partial view of the pneumatic circuit system 2. Here, FIG. 2 shows a plan view of the front surface 310 of the particle filter 31. The arrangements of the light sources 41, 42 and 43 around all particle filters 31, 32 and 33 are identical in each case, and so FIG. 2 is representative for the arrangement of all light sources 41, 42 and 43. The light sources 41, 42 and 43 shown in FIG. 2 are securely disposed at respectively equal distances from one another and, in respect of one type, opposite one another around the front surface 310 of the particle filter 31 in a common holder. This corresponds to an arrangement of the light sources 41, 42 and 43 in circumferential fashion in an alternating sequence with respect to the sorts thereof. A circumferentially uniform illumination of the front surface 310 and the back surface 311 of the particle filter 31, over the entire area thereof, ensures that all pathogens striking the particle filter 31 or passing through the particle filter 31 are exposed to the same, or at least approximately the same, radiance of the light emitted by the light sources 41, 42 and 43. The holder is designed to be removable from the piping 21 for simple maintenance. Consequently, an identical holder with light sources 41, 42 and 43 is respectively assigned to each light window 22. In this exemplary embodiment:

- the light sources of the first type 41 are embodied to emit light in a wavelength interval restricted to 385 nm to 425 nm, with an emission maximum at 405 nm,
- the light sources of the second type 42 are embodied to emit light in a wavelength interval restricted to 385 nm to 1000 nm, with an emission maximum at 600 or 630 nm, and
- the light sources of the third type 43 are embodied to emit light in a wavelength interval restricted to 900 nm to 1700 or 2000 nm, with a first emission maximum at 1300 or 1400 nm and a second emission maximum at 1550 or 1600 nm.

This ensures the excitation of all electrons and oscillator states of the microorganisms.

Figure 3A:
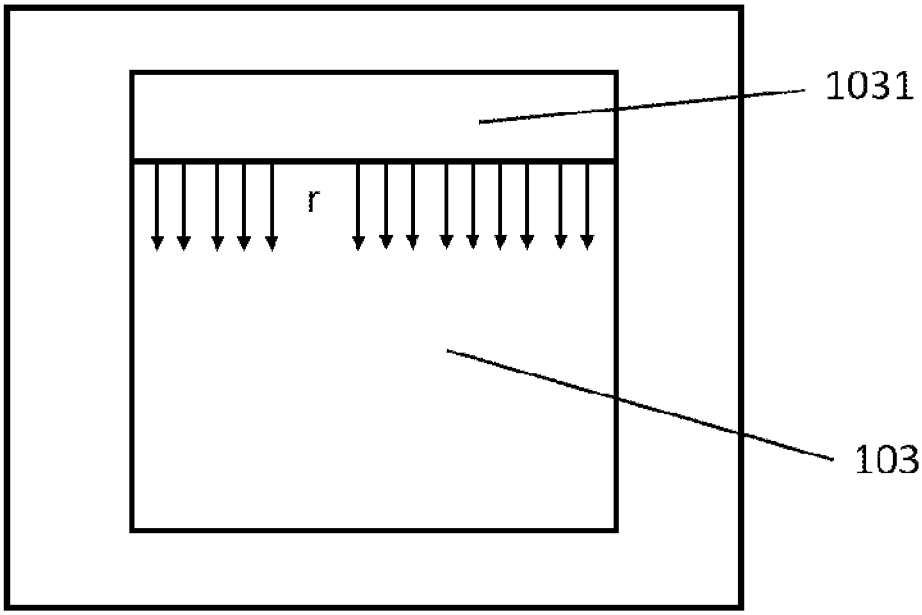
FIGS. 3*a* and 3*b* schematically show, in sections, an exemplary embodiment of the ventilator in which the light sources are disposed in such a way that the display area is irradiated.
Figure 3B:
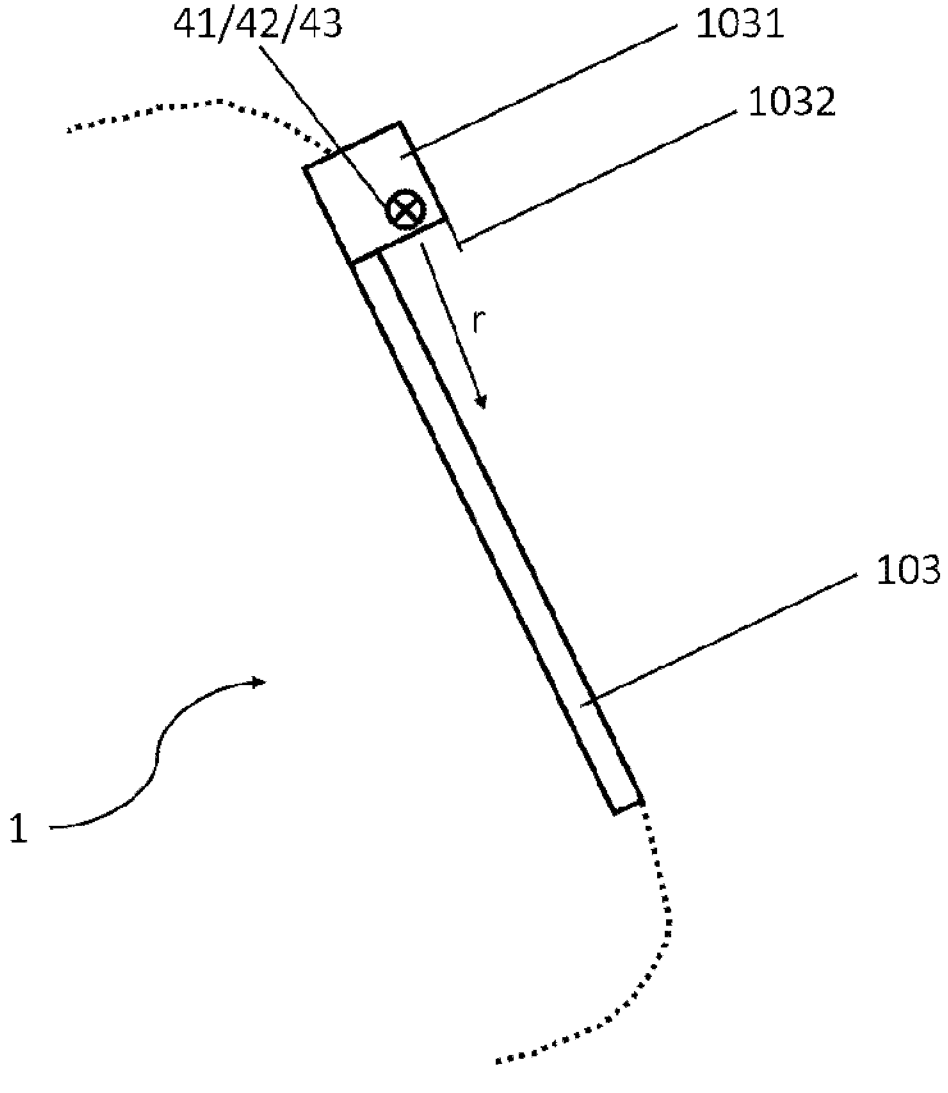

FIGS. 3*a* and 3*b* schematically show, in sections, an exemplary embodiment of the ventilator 1, in which the light sources 41, 42 and 43 are disposed in such a way that the display area 103 is irradiated. To this end, the light sources 41, 42 and 43 are disposed in a light source housing 1031, for example, and so the light sources are located above the display area. Consequently, it is possible for the emission direction r of the light sources 41, 42, 43 to strike the display area 103. In an exemplary embodiment, the light source housing 1031 comprises a type of screen 1032, which extends beyond the end of the light sources. As a result of this screen 1032, the display area 103 can be irradiated but the light sources 41, 42, 43 do not emit in the direction of persons gazing on the display area, for example. In a conceivable further exemplary embodiment, additional reflectors, not shown, are attached to the light source housing 1031 in such a way that the emission direction r of the light sources 41, 42, 43 is steered onto the display area 103, in particular. Particularly if the display area 103 is embodied as a touchscreen, on which the inputs, such as a variation in the ventilation pressure, for example, are set directly on the display area 103, it is advantageous if this surface can be sterilized by the light sources.

Figure 4:
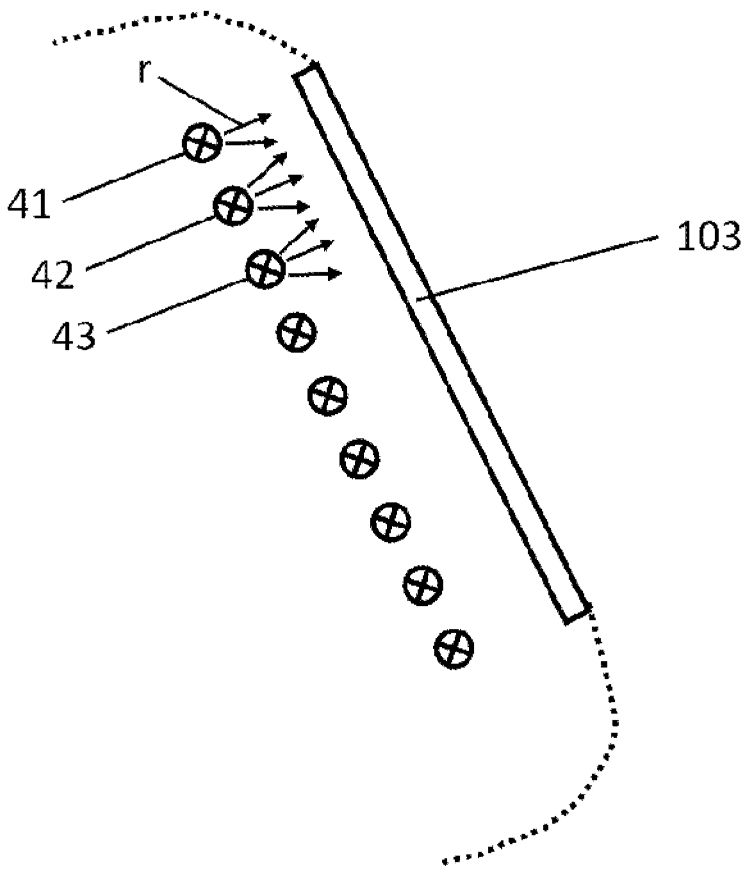
FIG. 4 schematically shows a section of an exemplary embodiment of the ventilator, in which the light sources are disposed in the interior of the ventilator behind the display area.

FIG. 4 schematically shows a section of an exemplary embodiment of the ventilator 1, in which the light sources 41, 42, 43 are disposed in the interior of the ventilator behind the display area 103. The light sources 41, 42, 43 are configured in such a way that the emission direction r radiates on the display area from the back. Advantageously, the display area 103 is configured in such a way, for example, that the radiation shines through the display area 103 and at least reaches the surface of the display area. In an exemplary embodiment, the light sources 41, 42, 43 simultaneously also serve as a background illumination for the display area 103 in addition to the sterilization of the surface of the display area. To this end, the display area 103 is embodied as an LCD, for example.

Figure 5:
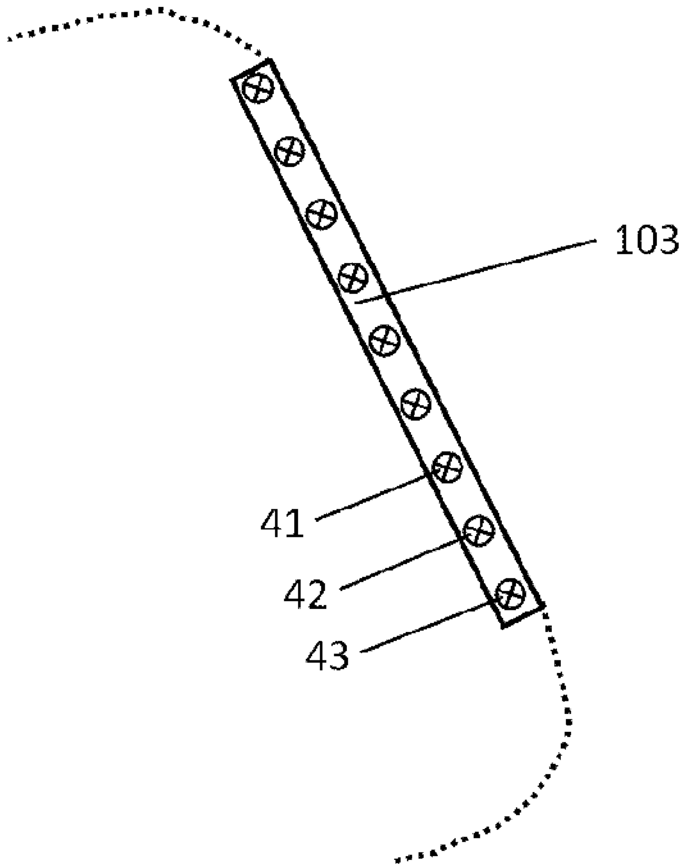
FIG. 5 shows an exemplary embodiment of the ventilator in sections, in which the light sources themselves are part of the display area.

FIG. 5 shows an exemplary embodiment of the ventilator 1 in sections, in which the light sources 41, 42 and 43 themselves are part of the display area 103. By way of example, the light sources can be embodied as organic light-emitting diodes and, together, yield an OLED display. Thus, the general advantages of an OLED display—space-saving structure and low power requirement—can be combined with the sterilizing effect of the chosen light sources.

FIGS. 6 to 9 illustrate exemplary embodiments of the ventilator 1, in which the light sources are disposed in the region of the respiratory gas outflow 102. In addition to the shown examples, combinations with the functional principle described in FIGS. 1 and 2, for example, are furthermore also possible. The exemplary embodiments of the partial sections, described in FIGS. 1 and 2, can be disposed, e.g., in front of the outlet 1025 within the ventilator 1 but downstream of the patient in the flow direction d. The embodiments described in FIGS. 6 to 9 relate, in particular, to ventilators in which the respiratory gas is guided back to the ventilator from the patient in a two-tube system, for example, and said respiratory gas is discharged from the ventilation system, for example by way of a respiratory gas outflow.

Figure 6A:
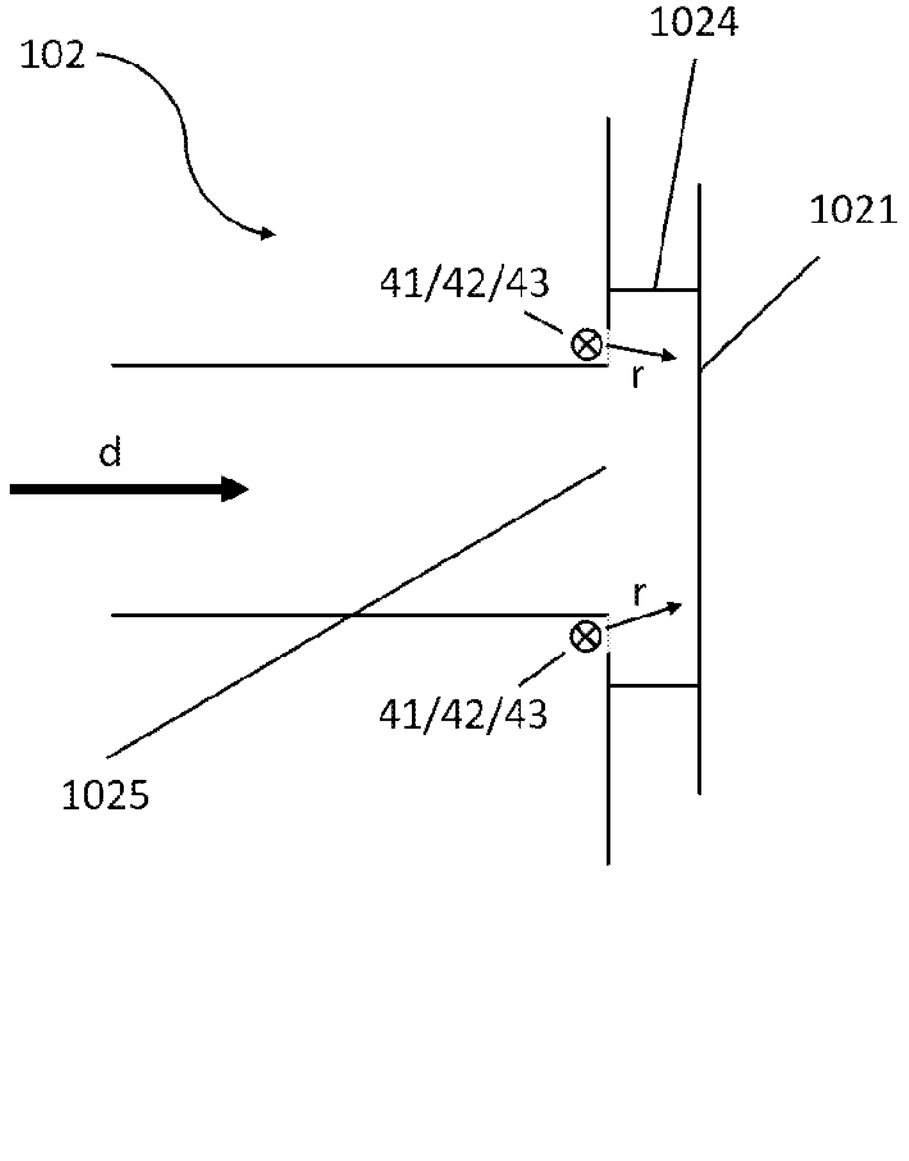
FIGS. 6*a* and 6*b* show the region of the respiratory gas outflow of the ventilator in exemplary fashion.
Figure 6B:
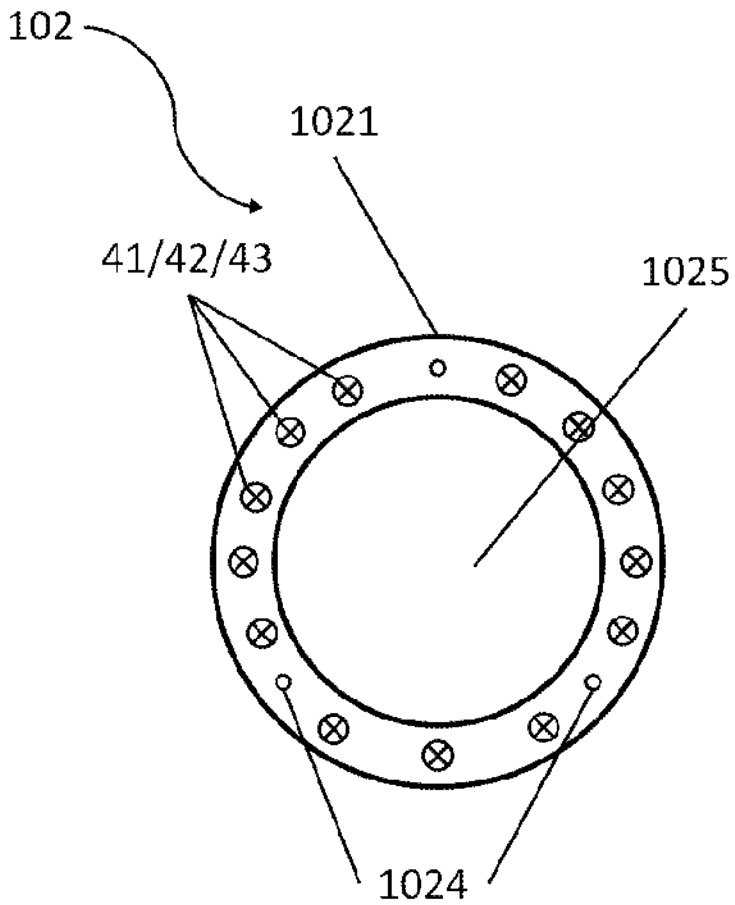

FIGS. 6*a* and 6*b* show the region of the respiratory gas outflow 102 of the ventilator 1 in exemplary fashion. A baffle 1021, which covers but does not seal the outlet 1025 of the respiratory gas outflow 102, for example, is disposed in the region of the respiratory gas outflow 102. To this end, the baffle 1021 is connected to the region of the respiratory gas outflow 102 at a distance from the outlet 1025 of the respiratory gas flow by connections 1024. By way of example, the connections 1024 are disposed in spaced apart fashion around the outlet 1025. Three connections 1024 are shown in exemplary fashion in FIG. 6*b*; however, more or fewer connections could also be disposed between the baffle 1021 and the region of the respiratory gas outflow 102. By way of example, the light sources 41, 42, 43 are disposed in the housing interior and around the outlet 1025 in the region of the respiratory gas outflow 102. Here, the light sources 41, 42, 43 can be disposed in such a way, for example, that the individual types of light sources are disposed in alternating fashion. That is to say, disposed next to a light source 41 there can be a light source 42 and, next, a light source 43. However, the sequence can also have any other structure. Additionally, the number of individual light source types need not have a uniform distribution—by way of example, twice as many light sources 41 could be present than light sources 42 and 43. Additionally, use could be made of only one or two types of light sources. In the region of the respiratory gas flow 102, the housing of the ventilator 1 has openings or light windows not described in any more detail such that the light sources 41, 42, 43 can radiate in the direction of the baffle 1021, for example. By way of example, the area of the baffle 1021 is greater than the cross-sectional area of the outlet 1025 and completely covers the outlet, as can be identified schematically in FIG. 6*b*.

By way of example, the baffle 1021 is configured in such a way that the ventilation gas flows with the flow direction d in the direction of the baffle 1021 and, in the process, strikes the baffle 1021. Firstly, this reduces the flow speed and secondly this may also lead to the accumulation on the surface of pathogens or germs from the ventilation gas. This renders it possible to lengthen the irradiation duration of the pathogens and leads to more effective sterilization. By way of example, the baffle 1021 can also be coated with silver or platinum-containing titanium oxide in order to obtain additional advantageous effects, as described in FIGS. 1 and 2.

In FIG. 6*a*, the baffle 1021 is disposed perpendicular to the flow direction d, for example. In other exemplary embodiments, the baffle 1021 can also have an inclined arrangement in relation to the flow direction d. In further embodiments, the baffle 1021 is embodied as a structured surface. In further embodiments, the baffle 1021 could also assume any other geometric form, such as a conical form, the form of a hemisphere or any free form. By way of example, the light sources 41, 42, 43 might also not be distributed around the outlet 1025, but only be disposed at points or on one side.

In a further embodiment, not shown in any more detail, an arrangement of particle filters, as described in FIG. 1 and FIG. 2, is disposed, for example, in the region of the respiratory gas outflow 102 instead of a baffle 1021.

According to the invention, particle filters could also be disposed on the baffle.

In all exemplary embodiments, the particle filters are configured and embodied to at least partly retain germs (viruses, bacteria, fungi). By way of example, said particle filters are additionally configured and embodied in all exemplary embodiments to at least partly transmit the light according to the invention or allow the latter to penetrate into deeper layers of the filter.

It should be understood that the number and arrangement of the light sources and of the baffle should predominantly reproduce the functional principle in exemplary fashion and both light sources and baffles may be present in different numbers, arrangements and forms.

Figure 7:
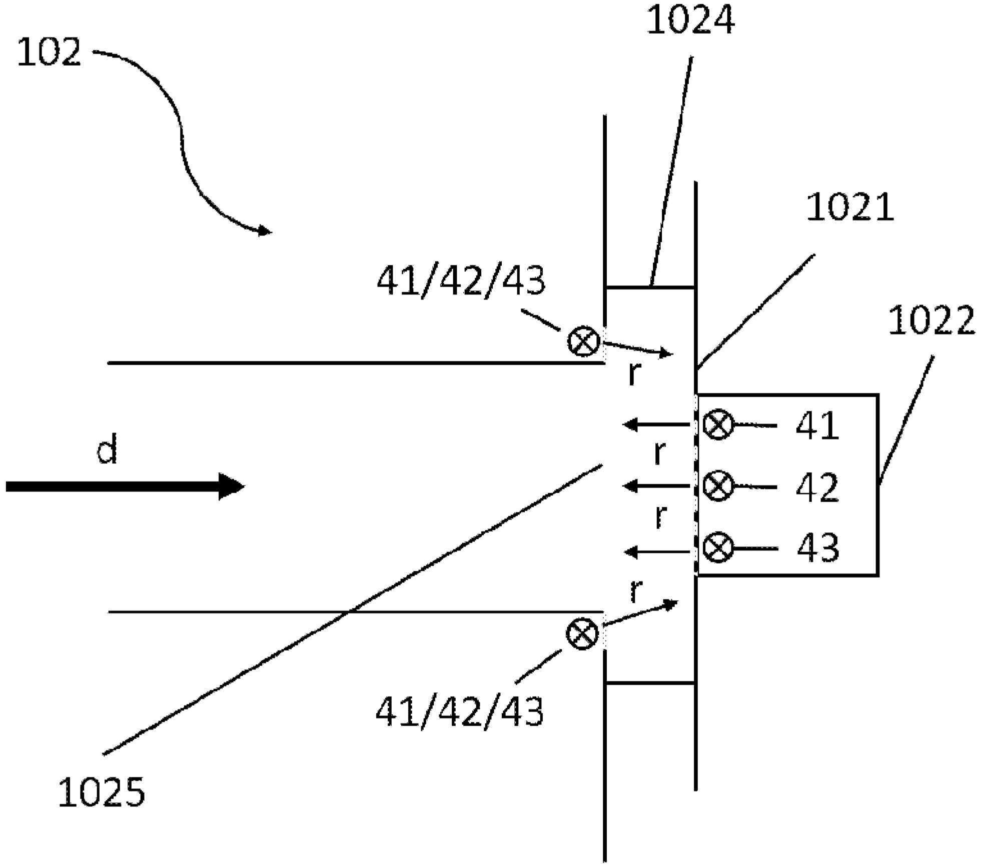
FIG. 7 shows a section of an exemplary embodiment of the ventilator in the region of the respiratory gas outflow.

FIG. 7 shows a section of an exemplary embodiment of the ventilator 1 in the region of the respiratory gas outflow 102. The basic elements and functionality are as described in FIG. 6. Additionally, further light sources 41, 42, 43 are disposed in a light source housing 1022, for example on the baffle as well. The light sources 41, 42, 43 are disposed and configured in such a way that the emission direction r is formed counter to the flow direction d. To this end, the baffle 1021 is configured and embodied in such a way that openings or, preferably, light windows are disposed in the region of the light sources. These additional light sources offer the advantage that, firstly, the ventilation gas (with pathogens contained therein) can already be irradiated over a distance in front of the outlet 1025. Secondly, the distance between the light sources and the baffle 1021 additionally reduces, and so the radiation intensity on the baffle 1021 can be additionally increased or, alternatively, light sources 41, 42, 43 with a weaker power can be used.

In a further exemplary embodiment, it is possible to dispense with the light sources on the side of the outlet 1025 and only dispose the light sources on the side of the baffle 1021.

Figure 8:
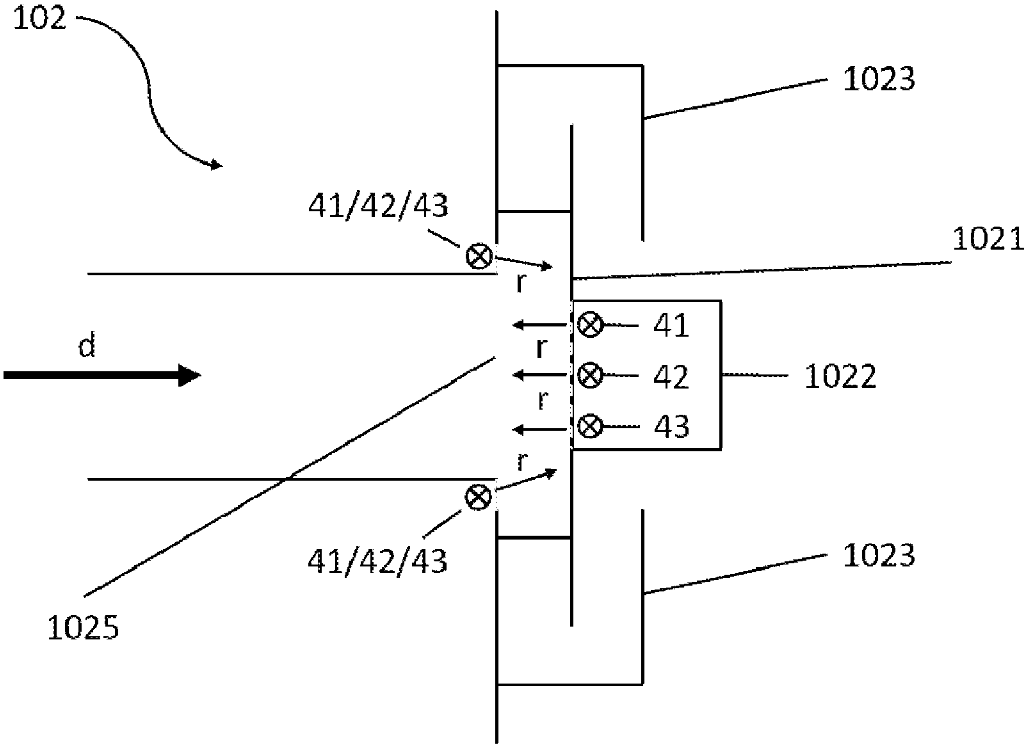
FIG. 8 shows a further exemplary embodiment of the ventilator in a section of the region of the respiratory gas outflow.

FIG. 8 illustrates a further exemplary embodiment of the ventilator 1 in a section of the region of the respiratory gas outflow 102. In addition to the exemplary embodiments illustrated in FIGS. 6*a, b* and FIG. 7, a type of wall 1023 is set up around the baffle 1021. By way of example, this wall 1023 is connected to the region of the respiratory gas outflow 102 and has an opening over the baffle. Here, the wall 1023 prevents radiation of the light sources 41, 42, 43 from also being perceivable outside of the appliance.

Figure 9:
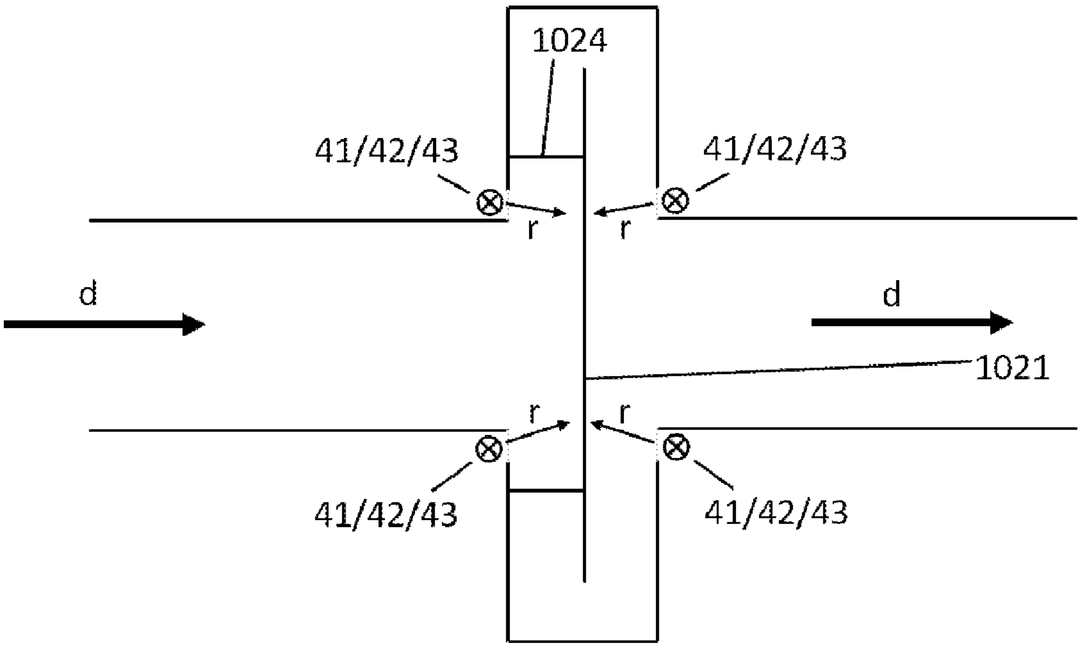
FIG. 9 shows a section of a further exemplary embodiment of the claimed ventilator.

FIG. 9 shows a section of a further exemplary embodiment of the ventilator 1. Here, the light sources 41, 42, 43 are disposed at a point within the housing, in the flow direction between the patient and the outlet 1025 in the region of the respiratory gas outflow 102. The general functional principle of the arrangement shown in FIG. 9 in exemplary fashion corresponds to the principle explained in FIGS. 1 and 2. In contrast to the embodiment described in FIGS. 1 and 2, only a baffle 1021 is introduced into the gas flow, said baffle slowing the gas flow down and serving as an accumulation surface for pathogens.

Figure 10:
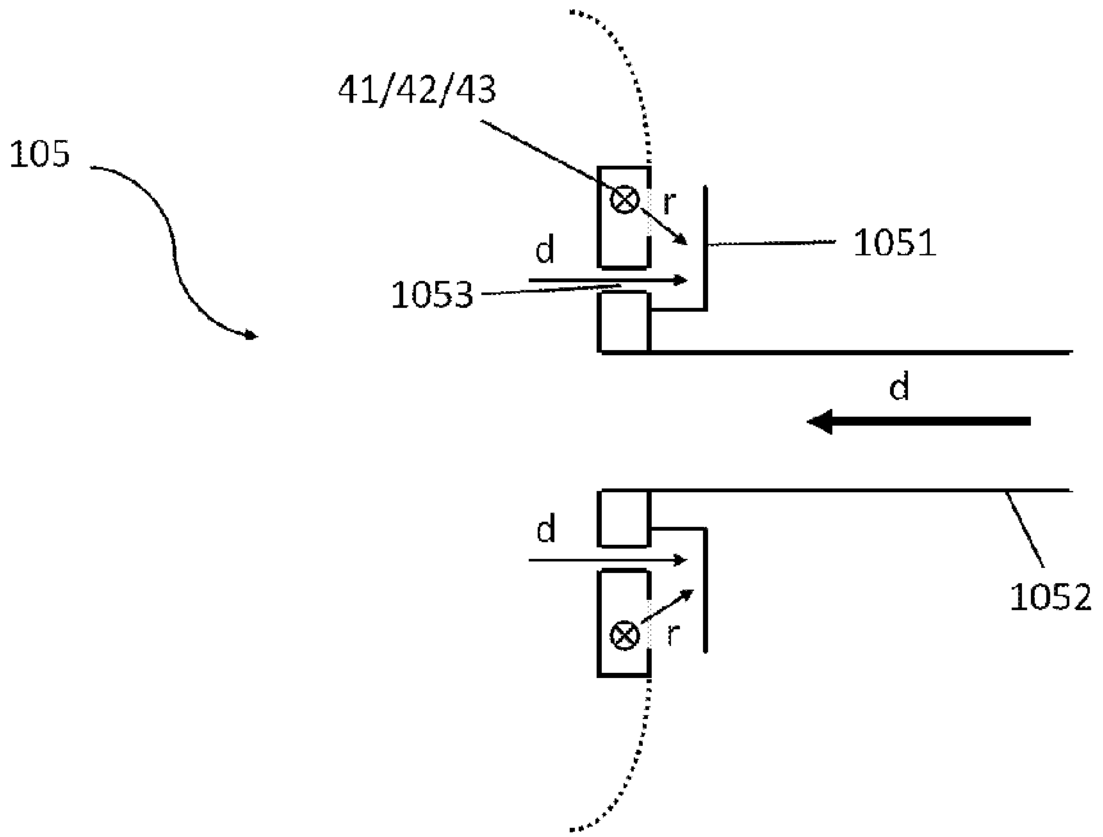
FIG. 10 shows an exemplary section of a patient interface of the claimed ventilator.

FIG. 10 shows an exemplary section of a patient interface 105 of the ventilator 1. The light sources 41, 42, 43 are disposed in exemplary fashion in the region of the outflow openings 1053. Covers 1051, for example, are attached downstream of the outflow openings 1053 in the flow direction d, said covers having a similar function or the same function to the baffles 1021 described in FIGS. 6-9. Here, the covers 1051 are connected to a part of the patient interface 105, for example. Ventilation gas is supplied to the patient through the gas supply line 1052. The ventilation gas expired by the patient leaves the patient interface through the outflow openings 1053, with the flow direction d, and strikes the cover 1051 in perpendicular fashion in the process. Here, the cover 1051 firstly serves as a location for slowing down the gas flow but also for at least temporary accumulation of pathogens and germs, which are irradiated and weakened or inactivated by the light sources 41, 42, 43. The inactivated or weakened germs or pathogens are regularly removed by the gas flow, and so no permanent accumulation occurs.

LIST OF REFERENCE NUMERALS

1 Ventilator
101 Air supply
102 Respiratory gas outflow
103 Display area
105 Patient interface
106 Gas flow line
107 Gas flow line
1021 Baffle
1022 Light source housing
1023 Wall
1024 Connections
1025 Outlet
1031 Light source housing
1032 Screen
1051 Cover
1052 Gas supply line
1053 Outflow opening
2 Pneumatic circuit system
21 Piping
22 Light window
31 Particle filter
32 Particle filter
33 Particle filter
310 Front surface
320 Front surface
330 Front surface
311 Back surface
321 Back surface
331 Back surface
41 Light source of a first type
42 Light source of a second type
43 Light source of a third type
6 Adapter
d Flow direction
r Light emission direction

What is claimed is:

1. A ventilator, wherein the ventilator comprises a pneumatic system for conveying ventilation gas in a flow direction (d) to a patient, at least two particle filters with a pore size respectively decreasing in the flow direction (d) disposed within the pneumatic system, and at least two light sources disposed first in the flow direction (d), followed by one of the at least two particle filters, light emitted by one of the at least two light sources comprising light having a wavelength within a range of from 385 nm to 780nm and light emitted by another one of the at least two light sources having a wavelength within a range of from greater than 780 nm to 2,000 nm, light emitted by any of the at least two light sources not comprising UVB and UVC light.

2. The ventilator of claim 1, wherein the ventilator comprises at least three particle filters with a pore size respectively decreasing in the flow direction (d) disposed within the pneumatic system.

3. The ventilator of claim 1, wherein at least one of the at least two particle filters is a glass frit having a pore width of from 1 um to 200 μm.

4. The ventilator of claim 1, wherein at least one of the at least two particle filters is present as a pellet made of glass wool.

5. The ventilator of claim 1, wherein at least one of the at least two light sources emits light in a wavelength range of from 385 nm to 425 nm with an emission maximum at 405 nm.

6. The ventilator of claim 1, wherein at least one of the at least two light sources emits light in a wavelength range of from 385 nm to 1000 nm with an emission maximum at 600 nm or at 630 nm.

7. The ventilator of claim 1, wherein at least one of the at least two light sources emits light in a wavelength range of from 900 nm to 2000 nm with a first emission maximum at 1300 nm or at 1400 nm and a second emission maximum at 1550 nm or at 1600 nm.

8. The ventilator of claim 7, wherein the at least one of the at least two light sources emits light in a wavelength range of from 900 nm to 1700 nm.

9. The ventilator of claim 5, wherein at least one of the at least two light sources emits light in a wavelength range of from 900 nm to 2000 nm with a first emission maximum at 1300 nm or 1400 nm and a second emission maximum at 1550 nm or 1600 nm.

10. The ventilator of claim 9, wherein the at least one of the at least two light sources emits light in a wavelength range of from 900 nm to 1700 nm.

11. The ventilator of claim 1, wherein the pneumatic system comprises at least one air supply to the ventilator and/or a respiratory gas outflow from the patient and/or a patient interface and/or a gas flow line.

12. The ventilator of claim 1, wherein the at least two light sources are disposed along a gas flow line.

13. The ventilator of claim 1, wherein at least one of the at least two light sources is disposed on each side of at least one of the at least two particle filters.

14. The ventilator of claim 1, wherein the pneumatic system is configured such that on at least one side of at least one of the at least two particle filters an entire area of the at least one of the at least two particle filters is illuminated.

15. The ventilator of claim 1, wherein a plurality of types of light sources are directed in circumferential fashion at at least one of the at least two particle filters in an alternating sequence with respect to light emitted by the light sources.

16. The ventilator of claim 1, wherein emitted light of the at least two light sources comprises a wavelength continuum of from 385 nm to 2,000 nm.

17. A ventilator, wherein the ventilator comprises a pneumatic system for conveying ventilation gas in a flow direction (d) to a patient, at least two particle filters with a pore size respectively decreasing in the flow direction (d) disposed within the pneumatic system, and one or more light sources disposed first in the flow direction (d), followed by one of the at least two particle filters, light emitted by at least one of the one or more light sources being light having a wavelength within a range of from 385 nm to 2000nm and a single emission maximum, light emitted by any of the one or more light sources not comprising UVB and UVC light, wherein the one or more light sources comprise a plurality of types of light sources directed in circumferential fashion at at least one of the at least two particle filters in an alternating sequence with respect to light emitted by the light sources.

18. The ventilator of claim 17, wherein the ventilator comprises at least three particle filters with a pore size respectively decreasing in the flow direction (d) disposed within the pneumatic system.

19. The ventilator of claim 17, wherein at least one light source of the one or more light sources is disposed on each side of the at least one partiele filter at least one of the at least two particle filters.

* * * * *